United States Patent
Depui et al.

(10) Patent No.: US 7,488,497 B2
(45) Date of Patent: *Feb. 10, 2009

(54) ORAL PHARMACEUTICAL DOSAGE FORMS COMPRISING A PROTON PUMP INHIBITOR AND A NSAID

(75) Inventors: Helene Depui, Göteborg (SE); Per Lundberg, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 187 days.

This patent is subject to a terminal disclaimer.

(21) Appl. No.: 10/620,000

(22) Filed: Jul. 14, 2003

(65) Prior Publication Data

US 2004/0022846 A1    Feb. 5, 2004

Related U.S. Application Data

(63) Continuation of application No. 10/090,882, filed on Mar. 4, 2002, now Pat. No. 6,613,354, which is a continuation of application No. 09/471,958, filed on Dec. 23, 1999, now Pat. No. 6,365,184, which is a continuation of application No. 08/793,078, filed as application No. PCT/SE96/01735 on Dec. 20, 1996, now abandoned.

(30) Foreign Application Priority Data

Jan. 8, 1996    (SE) ..................................... 9600070

(51) Int. Cl.
*A61K 9/24*    (2006.01)
*A61K 9/20*    (2006.01)

(52) U.S. Cl. .................... 424/472; 424/464; 424/470; 424/471

(58) Field of Classification Search ................. 424/464, 424/465, 472, 473, 481, 471, 468, 469, 470, 424/474, 493, 494, 490
See application file for complete search history.

(56) References Cited

U.S. PATENT DOCUMENTS

| 4,786,505 A | 11/1988 | Lovgren et al. ............. 424/468 |
| 5,417,980 A | 5/1995 | Goldman et al. ............ 424/464 |
| 5,518,730 A | 5/1996 | Fuisz |

(Continued)

FOREIGN PATENT DOCUMENTS

EP    0008780    8/1979

(Continued)

OTHER PUBLICATIONS

McCarthy, D.M. 1989 Gastroenterology 96:662-674, "Nonsteroidal Antiinflammatory Drug-Induced Ulcers . . . ".

(Continued)

*Primary Examiner*—Lakshmi S Channavajjala
(74) *Attorney, Agent, or Firm*—White & Case LLP

(57) ABSTRACT

An oral pharmaceutical dosage form comprising an acid susceptible proton pump inhibitor and one or more NSAIDs in a fixed formulation, wherein the proton pump inhibitor is protected by an enteric coating layer. The fixed formulation is in the form of an enteric coating layered tablet, a capsule or a multiple unit tableted dosage form. The multiple unit dosage forms are most preferred. The new fixed formulation is especially useful in the treatment of gastrointestinal side-effects associated with NSAID treatment.

28 Claims, 2 Drawing Sheets

U.S. PATENT DOCUMENTS

| | | | |
|---|---|---|---|
| 5,582,837 A | 12/1996 | Shell | |
| 5,651,987 A | 7/1997 | Fuisz | |
| 5,753,265 A | 5/1998 | Bergstrand et al. | 424/474 |
| 5,763,422 A | 6/1998 | Lichtenberger et al. | 514/78 |
| 5,817,338 A | 10/1998 | Bergstrand et al. | 424/474 |
| 5,955,451 A | 9/1999 | Lichtenberger et al. | 514/78 |
| 6,136,344 A * | 10/2000 | Depui et al. | 424/470 |
| 6,365,184 B1 | 4/2002 | DePui et al. | |
| 6,613,354 B2 | 9/2003 | Depui et al. | |

FOREIGN PATENT DOCUMENTS

| | | |
|---|---|---|
| EP | 0072021 | 8/1982 |
| EP | 0080341 | 11/1982 |
| EP | 0108295 | 10/1983 |
| EP | 0108504 | 10/1983 |
| EP | 0111103 | 10/1983 |
| EP | 0170752 | 12/1984 |
| EP | 0247983 | 12/1987 |
| EP | 0013566 | 1/1990 |
| EP | 0391518 | 2/1990 |
| EP | 0365947 | 5/1990 |
| EP | 0426479 | 5/1990 |
| EP | 0541369 | 11/1992 |
| EP | 0587220 | 8/1993 |
| EP | 0648487 | 10/1994 |
| GB | 2066070 | 12/1980 |
| GB | 2091097 | 11/1981 |
| GB | 2132887 | 11/1983 |
| GB | 2285989 | 1/1995 |
| JP | 08-301763 | 11/1996 |
| WO | 8501207 | 9/1984 |
| WO | 8503436 | 2/1985 |
| WO | 8702240 | 9/1986 |
| WO | 9312772 | 12/1992 |
| WO | 9403160 | 7/1993 |
| WO | 9404484 | 3/1994 |
| WO | 9412463 | 6/1994 |
| WO | 9509831 | 4/1995 |
| WO | 9510264 | 4/1995 |
| WO | 9530641 | 11/1995 |
| WO | 9725064 | 7/1997 |
| WO | 9822117 | 5/1998 |
| WO | 9822118 | 5/1998 |
| WO | 0166087 | 9/2001 |
| WO | 0222108 | 3/2002 |

OTHER PUBLICATIONS

Walan, A. Et al. 1989 "Effect of omeprazole and ranitine on ulcer healing . . . " The N.E. J. Med 320:69.

Guess, H.A. et al. 1988 "Fatal upper gastrointestinal hemorrhage or perforation . . . " J. Clin. Epidimol 41:35-45.

Larkai, E.N. et al. 1987 "Gastroduodenal mucosa and dyspeptic symptoms . . . " Am. J. Gastroenterology 82:1153.

Catford, J.C. et al. 1986 "Confidential inquiry into deaths from peptic ulcer . . . " Health Trends 18:37-41.

Hawkey C. "Non-steroidal anti-inflammatory drugs and peptic ulcers . . . " (1990) 300:278-284.

Scheiman, J.M. "Pathogenesis of gastroduodenal injury . . . " (1982) Semin. Arthritis Reheum. 21(4):201-210-.

Drug Facts and Comparisons 1994, pp. 1679-1684.

Remington: The Science and Practice of Pharmacy, chapter 93, 1650-1656, 1995.

Wan, L.S.C., "A Multiple-unit Tablet Formulation for Multi-layer Drug-coated Granules", S.T.P. PHARMA Sciences, 4(5)(1994), pp. 336-342.

Chem. Pharm. Bull., 42(11), 2327-2331 (1994).

Chem. Pharm. Bull., 44(7), 1361-1366 (1996).

* cited by examiner

ORAL PHARMACEUTICAL DOSAGE FORMS COMPRISING A PROTON PUMP INHIBITOR AND A NSAID

This application is a continuation of U.S. patent application Ser. No. 10/090,882, filed Mar. 4, 2002 now U.S. Pat. No. 6,613,354, which is a continuation of U.S. patent application Ser. No. 09/471,958, filed Dec. 23, 1999, now U.S. Pat. No. 6,365,184, issued Apr. 2, 2002, which is a continuation of U.S. patent application Ser. No. 08/793,078, filed Feb. 13, 1997, abandoned, which was the National Stage of International Application No. PCT/SE96/01735, filed Dec. 20, 1996.

FIELD OF THE INVENTION

The present invention is related to new oral pharmaceutical preparations especially for use in the treatment and prophylaxis of gastrointestinal disorders associated with the use of Non Steroidal Antiinflammatory Drugs (NSAIDs). The present preparations comprise an acid susceptible proton pump inhibitor in combination with one or more NSAID(s) in a new fixed unit dosage form, especially a tableted dosage form. Furthermore, the present invention refers to a method for the manufacture of such preparations and the use of such preparations in medicine.

BACKGROUND OF THE INVENTION

NSAIDs including acetyl salicylic acid are among the most commonly prescribed and used drugs world-wide. Despite the therapeutic benefits of NSAIDs, their use is frequently limited by an increased risk of gastrointestinal side-effects, mainly upper gastrointestinal side-effects like peptic ulceration and dyspeptic symptoms.

The relative risk of developing a gastric ulcer during NSAID treatment is increased by a factor 40-50, and the relative risk of developing a duodenal ulcer is increased by a factor 8-10 (McCarty D M. Gastroenterology 1989;96:662). The relative risk of developing an ulcer complication like bleeding and perforation of the stomach is increased by a factor 1.5-5 (Hawkey C. BMJ 1990;300:278). Further, dyspeptic symptoms are experienced in 30-60% of those on NSAID treatment (Larkai EN.AmJGas 1987;82:1153).

In the UK, NSAIDs account for 25% of all reports of adverse drug reactions received by the authorities, and the corresponding figure is 21% in USA. Therefore, therapies which avoid gastrointestinal side-effect caused by NSAIDs is requested.

Attempts to modify the NSAID structure in order to prevent such side-effects have so far been less successful. The most promising solution to the problem of healing and preventing NSAID associated upper gastrointestinal problems like ulcers and dyspeptic symptoms in patients with a need for continuous NSAID treatment is to combine the NSAID treatment with an anti-ulcer drug approved for the healing and/or prophylaxis of NSAID associated gastrointestinal side-effects such as prostaglandin analogues, $H_2$-receptor antagonists or proton pump inhibitors.

Established risk factors for developing NSAID associated upper gastrointestinal side-effects and complications are for instance high age, previous peptic ulcer and/or bleeding, high dose of NSAID, co-therapy with steroids, and co-therapy with anticoagulants. This means, that for example fragile and elderly patients tolerating a complication like bleeding or perforation badly, should receive prophylactic treatment in connection with their NSAID treatment.

NSAIDs are mainly used for the treatment of chronic diseases like rheumatoid arthritis and osteoarthritis, which are most often seen in the elderly population. Compliance is especially important in elderly and fragile patients, who have the highest risk of developing a life-threatening complication to NSAID treatment like bleeding or perforation. It is known that 50% of all peptic ulcer deaths occur in NSAID users and that 68% of these are >75 years old (Catford:Health Trends 1986;18:38). This is confirmed in another study concluding, that NSAID-related deaths occur primarily in those >75 years of age (Guess. J Cli Epidemiol 1988;41:35). The importance of compliance is further supported by the finding, that a majority of peptic ulcers associated with NSAID treatment are asymptomatic until the event.

Omeprazole being a well known proton pump inhibitor has been shown to be able to prevent gastric and duodenal erosions in healthy volunteers during treatment with acetyl salicylic acid. Clinical studies have shown, that omeprazole heals gastric as well as duodenal ulcers as fast and effectively in patients on continuous NSAID treatment as in non-NSAID users (Walan A. N Engl J Med 1989;320:69). These results have been the basis for an amendment to the dose recommendation for the use of omeprazole in healing of gastric and duodenal ulcers during continuous NSAID treatment approved by regulatory authorities in UK and Sweden.

Recent studies confirm, that omeprazole significantly reduces the risk of developing gastric ulcers, duodenal ulcers and also dyspeptic symptoms in patients on continuous NSAID treatment.

EP 0 426 479 describes tablet compositions comprising a NSAID such as ibuprofen and a gastric acid inhibiting drug, such as cimetidin etc. No specific arrangement is taken to avoid degradation if the gastric acid inhibitor is an acid susceptible compound, such as a proton pump inhibitor.

In proposed therapies comprising NSAID(s) and an acid susceptible proton pump inhibitor the different active substances are administered separately. It is well known that patient compliance is a main factor in receiving a good result in medical treatments. Therefore, administration of two or even more different tablets to the patient is not convenient or satisfactory to achieve the most optimal results. The present invention now provides new oral dosage forms comprising two or more different active substances combined in one fixed unit dosage form, preferably a tablet.

Some anti-ulcer drugs such as proton pump inhibitors are susceptible to degradation/transformation in acid reacting and neutral media as mentioned above. In respect of the stability properties, it is obvious that the one of the active substances being a proton pump inhibitor must be protected from contact with acidic gastric juice by an enteric coating layer. There are different enteric coating layered preparations of proton pump inhibitors described in the prior art, see for example U.S. Pat. No. 4,786,505 (AB Hässle) comprising omeprazole.

There are problems to produce a fixed unit dosage form comprising a rather high amount of active substance. Active substances with different physical properties combined in the same preparation give further problems. Preparation of a multiple unit tableted dosage form arises specific problems when enteric coating layered pellets containing the acid susceptible proton pump inhibitor are compressed into tablets. If the enteric coating layer does not withstand the compression of the pellets into a tablet, the susceptible active substance will be destroyed upon administration by penetrating acidic gastric juice, i.e. the acid resistance of the enteric coating layer of the pellets will not be sufficient in the tablet after compression.

SUMMARY OF THE INVENTION

The present invention provides oral, fixed unit dosage forms, i.e. multiple unit tableted dosage forms, enteric coating layered tablets, multilayered tablets or capsules filled with more than one pharmaceutically active compound. The active compounds are preferably an acid susceptible proton pump inhibitor in combination with one or more NSAIDs and wherein at least the proton pump inhibitor is protected by an enteric coated layer. These new dosage forms will simplify the regimen and improve the patient compliance.

DETAILED DESCRIPTION OF THE INVENTION

One object of the invention is to provide an oral, multiple unit tableted dosage form comprising an anti-ulcer drug, preferably an acid susceptible proton pump inhibitor in the form of individually enteric coating layered units, together with one or more NSAIDs and tablet excipients compressed into a tablet The enteric coating layer(s) covering the individual units of the acid susceptible proton pump inhibitor has properties such that the compression of the units into a tablet does not significantly affect the acid resistance of the individually enteric coating layered units. Furthermore, the multiple unit tableted dosage form provides a good stability to the active substances during long-term storage.

Alternatively, the prepared tablet has separate layers, one layer that comprises the acid susceptible proton pump inhibitor in the form of compressed enteric coated layered units and another layer that comprises the NSAID(s).

Figure 1:
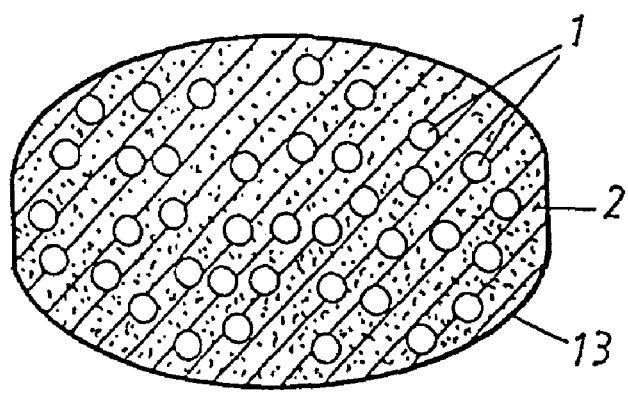
FIG. 1 illustrates a cross-section of a multiple unit tableted dosage form comprising an acid susceptible proton pump inhibitor in the form of enteric coating layered pellets (1) in admixture with a fast disintegrating granulate comprising a NSAID (2). The tablet is covered by an filmcoating layer (13).

The new fixed dosage form is preferably in the form of a multiple unit tableted dosage form comprising enteric coating layered units of the acid susceptible substance and the other active substance(s) in the granulated material constituting the rest of the compressed tablet, as shown in FIG. 1.

Figure 4:
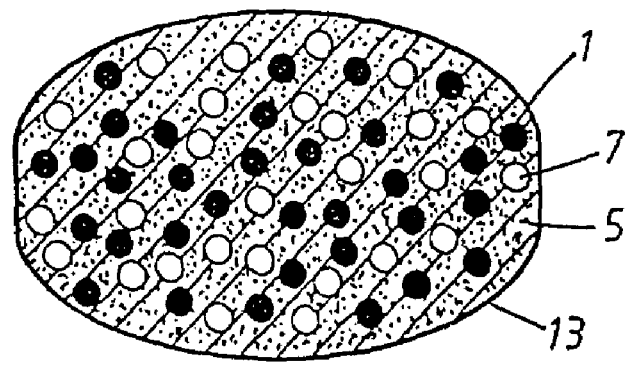
FIG. 4 illustrates a cross-section of a multiple unit tableted dosage form comprising an acid susceptible proton pump inhibitor in the form of enteric coating layered pellets (1) and a NSAID in the form of enteric coating layered pellets (7) in admixture with excipients (5). The tablet is covered by a filmcoating layer (13).
Figure 5:
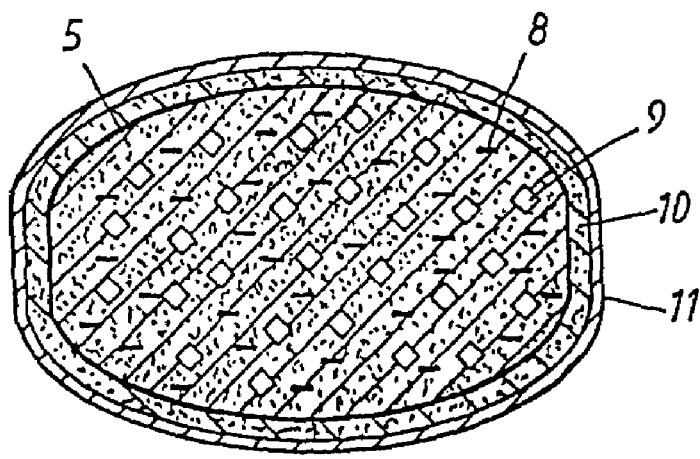
FIG. 5 illustrates a cross-section of an enteric coating layered tablet comprising an acid susceptible proton pump inhibitor (8) in admixture with one or more NSAID(s) (9) and excipients (5). The tablet is covered by an enteric coating layer (11) and optionally a separating layer (10) is layered in between the tablet core and the enteric coating layer.

Alternatively, the different active substances may be intimately mixed with each other and compressed into a conventional tablet, which is enteric coating layered, see FIG. 5, or both active substances are in the form of enteric coating layered pellets compressed into a multiple unit tableted formulation together with preferably fast disintegrating granules of inactive excipients, as exemplified in FIG. 4.

Figure 2:
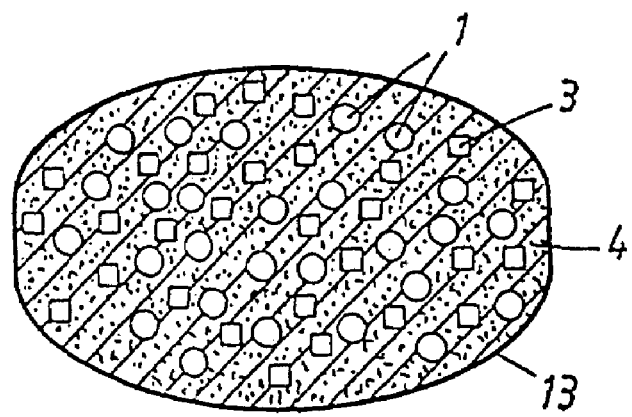
FIG. 2 illustrates a cross-section of a multiple unit tableted dosage form comprising an acid susceptible proton pump inhibitor in the form of enteric coating layered pellets (1) and a NSAID in the form of cyclodextrin complex (3) included in a fast disintegrating granulate (4). The tablet is covered by a filmcoating layer (13).
Figure 3:
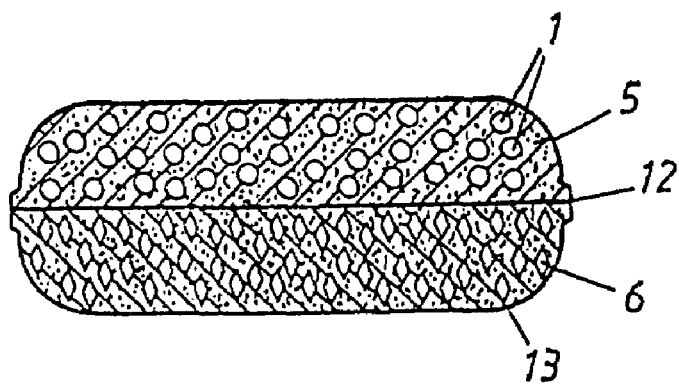
FIG. 3 illustrates a cross-section of a tablet with two separate layers, one layer comprises an acid susceptible proton pump inhibitor in the form of enteric coating layered pellets (1) in admixture with excipients (5) and the other layer comprises a NSAID (6) included in a gelling matrix giving extended release. The separate layers are optionally separated by a separating layer (12) and the tablet is covered by a filmcoating layer (13).
Figure 6:
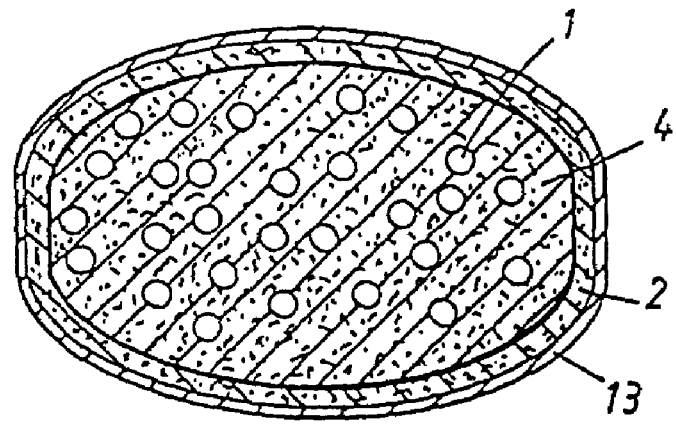
FIG. 6 illustrates a tablet comprising an acid susceptible proton pump inhibitor in the form of enteric coating layered pellets (1) in admixture with a fast disintegrating granulate (4) in a tablet core, surrounded by a coating layer comprising a NSAID substance/granulation (2). The tablet is covered by a pigmented filmcoating layer (13).

Further alternatives are exemplified as multiple unit dosage forms wherein the proton pump inhibitor is in the form of individually enteric coating layered units and the NSAID(s) in the form of a) a complex to obtain improved bioavailability, see FIG. 2, or b) in the form of a gelling matrix resulting in a preparation with extended release of the NSAID(s), see FIG. 3. A further alternative is a multiple dosage form with the proton pump inhibitor in the form of individually enteric coating layered units compressed into a tablet and thereupon a separate layer of the NSAID(s) is applied by spray layering on the tablet. The tablet is covered by a pigmented filmcoating layer to protect the NSAID(s), see FIG. 6, because some NSAID(s) are light sensitive and require a light protecting layer.

In still another alternative, the different active substances are dry mixed and filled into a capsule. In the latter preparation the acid susceptible proton pump inhibitor is in the form of enteric coating layered units and the NSAID(s) is/are in the form of granules or alternatively in the form of modified release formulated units such as enteric coating layered units or units layered with a controlled release layer.

The NSAID(s) may be formulated in instant release, sustained release or extended release formulations. Alternatively, the components may be formulated in an effervescent formulation. Furthermore, as some NSAID(s) are light sensitive the formulation is preferably light protected by a pigmented tablet filmcoating layer, as exemplified in FIG. 6, or by including a pigment in one of the coating layers to be applied on the tableted dosage form.

A further object of the invention is to provide a dosage form which is divisible, such as divisible tablets.

Still a further object of the invention is to provide a multiple unit tableted dosage form, which is divisible and easy to handle. Some of the multiple unit tableted dosage forms may be dispersed in a slightly acidic aqueous liquid and can be given to patients with swallowing disorders and in pediatrics. Such a suspension of dispersed units/pellets of appropriate size can be used for oral administration and also for feeding through a naso-gastric tube.

The different active components used in the present dosage forms are defined below.

Active Substances

The anti-ulcer drug is preferably an acid susceptible proton pump inhibitor. Such proton pump inhibitors are for example compounds of the general formula I

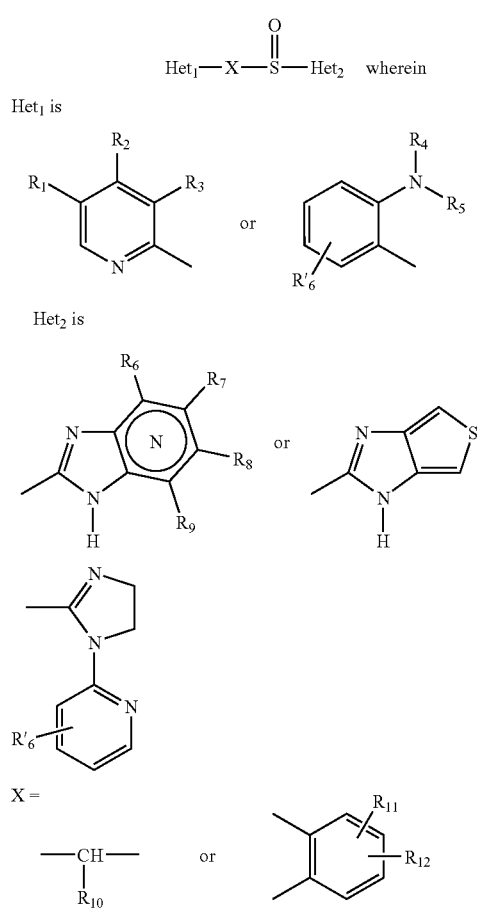

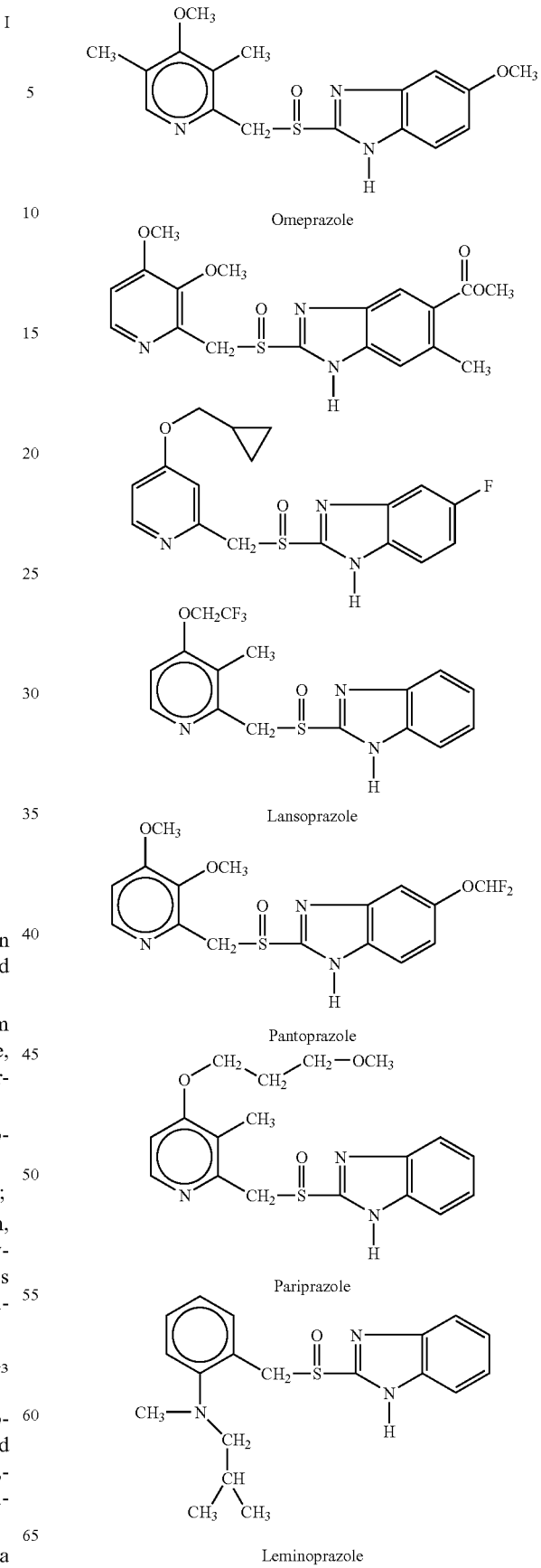

wherein

N in the benzimidazole moiety means that one of the carbon atoms substituted by $R_6$-$R_9$ optionally may be exchanged for a nitrogen atom without any substituents;

$R_1$, $R_2$ and $R_3$ are the same or different and selected from hydrogen, alkyl, alkoxy optionally substituted by fluorine, alkylthio, alkoxyalkoxy, dialkylamino, piperidino, morpholino, halogen, phenyl and phenylalkoxy;

$R_4$ and $R_5$ are the same or different and selected from hydrogen, alkyl and aralkyl;

$R_6'$ is hydrogen, halogen, trifluoromethyl, alkyl and alkoxy;

$R_6$-$R_9$ are the same or different and selected from hydrogen, alkyl, alkoxy, halogen, haloalkoxy, alkylcarbonyl, alkoxycarbonyl, oxazolyl, trifluoroalkyl, or adjacent groups $R_6$-$R_9$ form ring structures which may be further substituted;

$R_{10}$ is hydrogen or forms an alkylene chain together with $R_3$ and $R_{11}$ and $R_{12}$ are the same or different and selected from hydrogen, halogen or alkyl, alkyl groups, alkoxy groups and moities thereof, they may be branched or straight $C_1$-$C_9$-chains or comprise cyclic alkyl groups, such as cycloalkylalkyl.

Examples of proton pump inhibitors according to formula I are

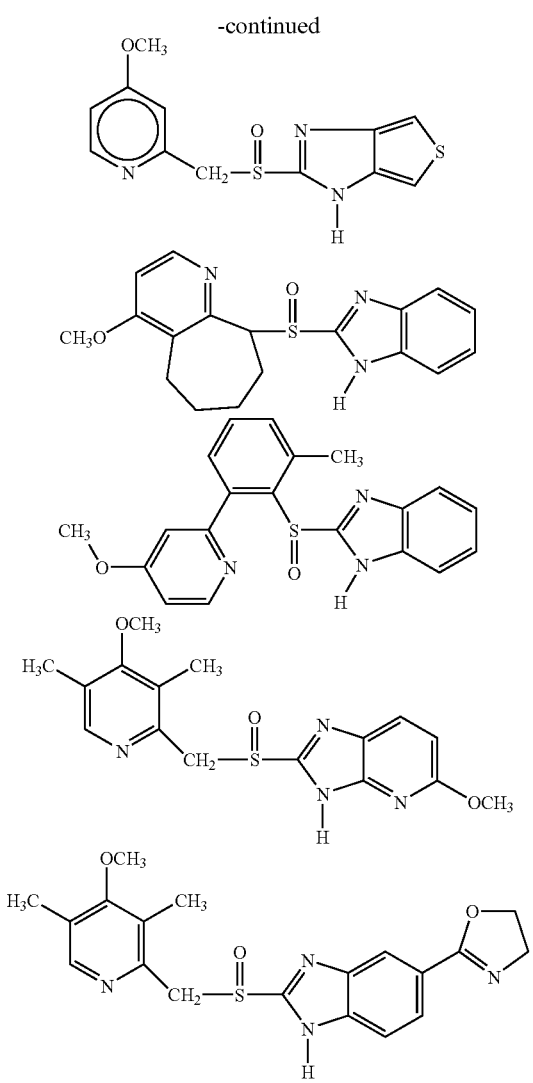

The acid susceptible proton pump inhibitors used in the dosage forms of the invention may be used in their neutral form or in the form of an alkaline salt, such as for instance the $Mg^{2+}$, $Ca^{2+}$, $Na^+$, $K^+$ or $Li^+$ salts, preferably the $Mg^{2+}$ salts. Further where applicable, the compounds listed above may be used in racemic form or in the form of the substantially pure enantiomer thereof, or alkaline salts of the single enantiomers.

Suitable proton pump inhibitors are for example disclosed in EP-A1-0005129, EP-A1-174 726, EP-A1-166 287, GB 2 163 747 and WO90/06925, WO91/19711, WO91/19712, and further especially suitable compounds are described in WO95/01977 and WO94/27988.

A wide variety of NSAIDs may be used in combination with a suitable proton pump inhibitor and optional pharmaceutically acceptable excipients in the fixed unit dosage form according to the present invention. Such NSAIDs include for example propionic acid derivatives, oxicams, acetic acid and acetamide derivatives, salicylic acid derivatives and pyrazolidine derivatives.

Also future NSAIDs like cyclooxygenase (COX) 2 selective NSAIDs and NO-releasing NSAIDs (de Soldato P, NO-releasing NSAID:s, A new class of safer anti-inflammatory analgesic and anti-pyrretic agents; The IV International meeting on side-effects of anti-inflammatory drugs Aug. 7-9, 1995) may be included.

In the following examples of some suitable NSAIDs are listed: Acetyl salicylic acid, indometacin, diclofenac, piroxicam, tenoxicam, ibuprofen, naproxen, ketoprofen, nabumetone, ketorolac, azapropazone, mefenamic acid, tolfenamic acid, sulindac, diflunisal, tiaprofenic acid, podophyllotoxin derivatives, acemetacin, aceclofenac, droxicam, oxaprozin, floctafenine, phenylbutazone, proglumetacin, flurbiprofen, tolmetin and fenbufen.

The active NSAIDs could be in standard forms or used as salts, hydrates, esters etc. A combination of two or more of the above listed drugs may be used. Preferable NSAIDs for the new fixed dosage form are diclofenac, ibuprofen, naproxen and piroxicam.

The preferred multiple unit tableted dosage form comprising a proton pump inhibitor (in the form of a racemat, an alkaline salt or one of its single enantiomers) and one or more NSAIDs, is characterized in the following way. Individually enteric coating layered units (small beads, granules or pellets) containing the proton pump inhibitor and optionally containing alkaline reacting substances, are mixed with the NSAID(s) and conventional tablet excipients. Preferably, the NSAID(s) and tablet excipients are in the form of a granulation. The dry mixture of enteric coating layered units, NSAID granules and optional excipients are compressed into multiple unit tableted dosage forms. With the expression "individual units" is meant small beads, granules or pellets, in the following referred to as pellets of the acid susceptible proton pump inhibitor.

The compaction process (compression) for formulating the multiple unit tableted dosage form must not significantly affect the acid resistance of the enteric coating layered pellets comprising the acid susceptible proton pump inhibitor. In other words the mechanical properties, such as the flexibility and hardness as well as the thickness of the enteric coating layer(s), must secure that the requirements on enteric coated articles in the United States Pharmacopeia are accomplished in that the acid resistance does not decrease more than 10% during the compression of the pellets into tablets.

The acid resistance is defined as the amount of proton pump inhibitor in the tablets or pellets after being exposed to simulated gastric fluid USP, or to 0, 1 M HCl (aq) relative to that of unexposed tablets and pellets, respectively. The test is accomplished in the following way. Individual tablets or pellets are exposed to simulated gastric fluid of a temperature of 37° C. The tablets disintegrate rapidly and release the enteric coating layered pellets to the medium. After two hours the enteric coating layered pellets are removed and analyzed for content of the proton pump inhibitor using High Performance Liquid Chromatography (HPLC).

Further specific components which may be used in the fixed unit dosage forms of the present invention are defined below.

Core Material—for Enteric Coating Layered Pellets/Units

The core material for the individually enteric coating layered pellets can be constituted according to different principles. Seeds layered with the proton pump inhibitor, optionally mixed with alkaline substances, can be used as the core material for the further processing.

The seeds which are to be layered with the proton pump inhibitor can be water insoluble seeds comprising different oxides, celluloses, organic polymers and other materials, alone or in mixtures or water-soluble seeds comprising different inorganic salts, sugars, non-pareils and other materials, alone or in mixtures. Further, the seeds may comprise the proton pump inhibitor in the form of crystals, agglomerates, compacts etc. The size of the seeds is not essential for the present invention but may vary between approximately 0.1 and 2 mm. The seeds layered with the proton pump inhibitor are produced either by powder or solution/suspension layering using for instance granulation or spray coating layering equipment.

Before the seeds are layered, the proton pump inhibitor may be mixed with further components. Such components can be binders, surfactants fillers, disintegrating agents, alkaline additives or other and/or pharmaceutically acceptable ingredients alone or in mixtures. The binders are for example polymers such as hydroxypropyl methylcellulose (HPMC), hydroxypropyl-cellulose (HPC), carboxymethylcellulose sodium, polyvinyl pyrrolidone (PVP), or sugars, starches or other pharmaceutically acceptable substances with cohesive properties. Suitable surfactants are found in the groups of pharmaceutically acceptable non-ionic or ionic surfactants such as for instance sodium lauryl sulfate.

Alternatively, the proton pump inhibitor optionally mixed with alkaline substances and further mixed with suitable constituents can be formulated into a core material. Said core material may be produced by extrusion/spheronization, balling or compression utilizing conventional process equipment. The size of the formulated core material is approximately between 0.1 and 4 mm and preferably between 0.1 and 2 mm. The manufactured core material can further be layered with additional ingredients comprising the proton pump inhibitor and/or be used for further processing.

The proton pump inhibitor is mixed with pharmaceutical constituents to obtain preferred handling and processing properties and a suitable concentration of the proton pump inhibitor in the final preparation. Pharmaceutical constituents such as fillers, binders, lubricants, disintegrating agents, surfactants and other pharmaceutically acceptable additives may be used.

Further, the proton pump inhibitor may also be mixed with an alkaline, pharmaceutically acceptable substance (or substances). Such substances can be chosen among, but are not restricted to substances such as the sodium, potassium, calcium, magnesium and aluminum salts of phosphoric acid, carbonic acid, citric acid or other suitable weak inorganic or organic acids; aluminum hydroxide/sodium bicarbonate coprecipitate; substances normally used in antacid preparations such as aluminum, calcium and magnesium hydroxides; magnesium oxide or composite substances, such as $Al_2O_3.6MgO.CO_2.12H_2O$, $(Mg_6Al_2(OH)_{16}CO_3.4H_2O)$, $MgO.Al_2O_3.2SiO_2.nH_2O$ or similar compounds; organic pH-buffering substances such as trihydroxymethylaminomethane, basic amino acids and their salts or other similar, pharmaceutically acceptable pH-buffering substances.

Alternatively, the aforementioned core material can be prepared by using spray drying or spray congealing technique.

Enteric Coating Layer(s)

Before applying the enteric coating layer(s) onto the core material in the form of individual pellets, the pellets may optionally be covered with one or more separating layer(s) comprising pharmaceutical excipients optionally including alkaline compounds such as pH-buffering compounds. This/these separating layer(s), separate(s) the core material from the outer layers being enteric coating layer(s). This/these separating layer(s) protecting the core material of proton pump inhibitor should be water soluble or rapidly disintegrating in water.

The separating layer(s) can be applied to the core material by coating or layering procedures in suitable equipments such as coating pan, coating granulator or in a fluidized bed apparatus using water and/or organic solvents for the coating process. As an alternative the separating layer(s) can be applied to the core material by using powder coating technique. The materials for the separating layers are pharmaceutically acceptable compounds such as, for instance, sugar, polyethylene glycol, polyvinylpyrrolidone, polyvinyl alcohol, polyvinyl acetate, hydroxypropyl cellulose, methylcellulose, ethylcellulose, hydroxypropyl methyl cellulose, carboxymethylcellulose sodium, water soluble salts of enteric coating polymers and others, used alone or in mixtures. Additives such as plasticizers, colorants, pigments, fillers anti-tacking and anti-static agents, such as for instance magnesium stearate, titanium dioxide, talc and other additives may also be included into the separating layer(s).

When the optional separating layer, is applied to the core material it may constitute a variable thickness. The maximum thickness of the separating layer(s) is normally only limited by processing conditions. The separating layer may serve as a diffusion barrier and may act as a pH-buffering zone. The pH-buffering properties of the separating layer(s) can be further strengthened by introducing into the layer(s) substances chosen from a group of compounds usually used in antacid formulations such as, for instance, magnesium oxide, hydroxide or carbonate, aluminum or calcium hydroxide, carbonate or silicate; composite aluminum/magnesium compounds such as, for instance $Al_2O_3.6MgO.CO_2.12H_2O$, $(Mg_6Al_2(OH)_{16}CO_3.4H_2O)$, $MgO.Al_2O_3.2SiO_2.nH_2O$, aluminum hydroxide/sodium bicarbonate coprecipitate or similar compounds; or other pharmaceutically acceptable pH-buffering compounds such as, for instance the sodium, potassium, calcium, magnesium and aluminum salts of phosphoric, carbonic, citric or other suitable, weak, inorganic or organic acids; or suitable organic bases, including basic amino acids and salts thereof. Talc or other is compounds may be added to increase the thickness of the layer(s) and thereby strengthen the diffusion barrier. The optionally applied separating layer(s) is not essential for the invention. However, the separating layer(s) may improve the chemical stability of the active substance and/or the physical properties of the novel multiple unit tableted dosage form.

Alternatively, the separating layer may be formed in situ by a reaction between an enteric coating polymer layer applied on the core material and an alkaline reacting compound in the core material. Thus, the separating layer formed comprises a water soluble salt formed between the enteric coating layer polymer(s) and an alkaline reacting compound which is in the position to form a salt.

One or more enteric coating layers are applied onto the core material or onto the core material covered with separating layer(s) by using a suitable coating technique. The enteric coating layer material may be dispersed or dissolved in either water or in suitable organic solvents. As enteric coating layer polymers one or more, separately or in combination, of the following can be used, e.g. solutions or dispersions of methacrylic acid copolymers, cellulose acetate phthalate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating polymer(s).

The enteric coating layers contain pharmaceutically acceptable plasticizers to obtain the desired mechanical properties, such as flexibility and hardness of the enteric coating layers. Such plasticizers are for instance, but not restricted to triacetin, citric acid esters, phthalic acid esters, dibutyl sebacate, cetyl alcohol, polyethylene glycols, polysorbates or other plasticizers.

The amount of plasticizer is optimized for each enteric coating layer formula, in relation to selected enteric coating layer polymer(s), selected plasticizer(s) and the applied amount of said polymer(s), in such a way that the mechanical properties, i.e. flexibility and hardness of the enteric coating layer(s), for instance exemplified as Vickers hardness, are adjusted so that the acid resistance of the pellets covered with enteric coating layer(s) does not decrease significantly during compression of pellets into tablets. The amount of plasticizer is usually above 10% by weight of the enteric coating layer polymer(s), preferably 15-50% and more preferably 20-50%. Additives such as dispersants, colorants, pigments polymers e.g. poly (ethylacrylat, methylmethacrylat), anti-tacking and anti-foaming agents may also be included into the enteric coating layer(s). Other compounds may be added to increase film thickness and to decrease diffusion of acidic gastric juices into the acid susceptible material. To protect the acid susceptible substance, the proton pump inhibitor, and to obtain an acceptable acid resistance of the dosage form according to the invention, the enteric coating layer(s) constitutes a thickness of approximately at least 10 µm, preferably more than 20 µm. The maximum thickness of the applied enteric coating is normally only limited by processing conditions and the desired dissolution profile.

The enteric coating layer may also be used for layering of the NSAID(s). Alternatively, the enteric coating layer described above may also be used for an enteric coating layer of conventional tablets comprising a composition of a proton pump inhibitor and one or more NSAIDs, optionally the prepared tablet core also is covered by one of the separating layers described above to separate the tablet core from the enteric coating layer.

Over-Coating Layer

Pellets covered with enteric coating layer(s) may further be covered with one or more over-coating layer(s). The over-coating layer(s) should be water soluble or rapidly disintegrating in water. The over-coating layer(s) can be applied to the enteric coating layered pellets by coating or layering procedures in suitable equipments such as coating pan, coating granulator or in a fluidized bed apparatus using water and/or organic solvents for the coating or layering process. The materials for over-coating layers are chosen among pharmaceutically acceptable compounds such as, for instance sugar, polyethylene glycol, polyvinylpyrrolidone, polyvinyl alcohol, polyvinyl acetate, hydroxypropyl cellulose, methylcellulose, ethylcellulose, hydroxypropyl methyl cellulose, carboxymethylcellulose sodium and others, used alone or in mixtures. Additives such as plasticizers, colorants, pigments, fillers, anti-tacking and anti-static agents, such for instance magnesium stearate, titanium dioxide, talc and other additives may also be included into the over-coating layer(s). Said over-coating layer may further prevent potential agglomeration of enteric coating layered pellets, further it may protect the enteric coating layer towards cracking during the compaction process and enhance the tableting process. The maximum thickness of the applied over-coating layer(s) is normally limited by processing conditions and the desired dissolution profile. The over-coating layer may also be used as a tablet filmcoating layer.

NSAID Preparation

The active substance(s) in the form of one or more NSAID substances is dry mixed with inactive excipients, wherein one or more of the excipients optionally is a disintegrant. The mixture is wet massed with a granulation liquid. The wet mass is dried preferably to a loss on drying of less than 3% by weight Thereafter the dry mass is milled to a suitable size for the granules, such as smaller than 4 mm, and preferably smaller than 1 mm. Suitable inactive excipients for the NSAID granulation are for instance, sodium starch glycolate, corn starch, crosslinked polyvinylpyrrolidone, low substituted hydroxypropyl cellulose, microcrystalline cellulose, mannitol and colloidal silicon dioxide an hydrous (Aerosil®) and the like. The dry mixture comprising NSAID(s) is mixed with a suitable granulation liquid comprising for instance, polyvinyl pyrrolidone, hydroxypropyl-cellulose, polyethylene glycol, hydroxypropyl cellulose and optionally wetting agents, such as sodium lauryl sulphate, dissolved in purified water or a suitable alcohol or a mixture thereof.

Mechanical treatment may in some cases be used to form a complex between the NSAID(s) and a complex forming agent, such as beta-hydroxypropyl cyclodextrin like in Example 3 below. Cyclodextrin complexes of NSAID(s) are shown to have an increased bioavailability of the NSAID(s), see for instance Drug Dev. Ind. Pharm. 19(7), 843-852, (1993).

Further, the NSAID may be mixed with a gelling agent during the granulation, such as hydrophilic polymer(s). Suitable gelling hydrophilic polymers are for instance hydroxypropylmethylcellulose, polyoxyethylen (polyethylene glycol), hydroxypropylcellulose, hydroxyethylcellulose and xantan. The granules may also comprise buffering substances. See for instance Example 4 below. Some NSAIDs irritate the gastric mucosa and benefit from a protecting enteric coating layer and may be formulated as enteric coating layered pellets.

Multiple Unit Tablets

The enteric coating layered pellets comprising a proton pump inhibitor are mixed with the granules comprising NSAID(s) and tablet excipients. The mixture is compressed into a multiple unit tableted dosage form. The compressed tablet is optionally covered with a filmforming agent(s) to obtain a smooth surface of the tablet and further enhance the stability of the tablet during packaging and transport Such a tablet filmcoating layer may further comprise additives such as anti-tacking agents, colorants and pigments or other additives to obtain a tablet of good appearance and with a light-protection for light sensitive components.

The enteric coated pellets with or without an over-coat and the NSAID granules are mixed with tablet excipients such as fillers, binders, disintegrants, lubricants and other pharmaceutically acceptable additives and compressed into tablets. Suitable lubricants for the tableting process are for instance sodium stearyl fumarate, magnesium stearate and talc.

Alternatively, the NSAID(s) may be dry mixed with the enteric coating layered pellets comprising the proton pump inhibitor optionally together with inactive excipients and compressed into tablets (direct compression), or the different active substances may be formulated in different layers, optionally the NSAID(s) in the form of a layer with a controlled release.

Further, both the NSAID(s) and the proton pump inhibitor in the form of enteric coating layered pellets may be mixed with inactive tablet excipients and compressed into a tablet. The compressed tablet is optionally covered by a tablet filmcoating layer to obtain a tablet of good appearance.

As a further alternative a multiple unit tableted dosage form comprising the proton pump inhibitor is spray coating layered by a suspension or solution comprising the NSAID(s). The prepared tablet is thereafter covered by a pigmented tablet filmcoating layer.

The fraction of enteric coating layered pellets constitutes less than 75% by weight of the total tablet weight and preferably less than 60%. By increasing the amount of the granules comprising the NSAID(s) the fraction of enteric coating layered proton pump inhibitor pellets in the multiple unit dosage form may be reduced. By choosing small enteric coating layered pellets in the formulation according to the present invention, the number of pellets in each tablet can be held high which in turn makes the tablet divisible with retained dosing accuracy.

Thus, the preferred multiple unit tablet formulation consists of enteric coating layered pellets containing one active substance in the form of an acid susceptible proton pump inhibitor, optionally mixed with alkaline reacting compound(s), compressed into tablet together with granules containing NSAID(s) and optionally tablet excipients. The addition of an alkaline reacting material to the proton pump inhibitor is not necessary, in any sense but such a substance may further enhance the stability of the proton pump inhibitor or some of the alkaline reacting compounds may react in situ with the enteric coating material to form a separating layer. The enteric coating layer(s) is making the pellets of the dosage form insoluble in acidic media, but disintegrating/dissolving in near neutral to alkaline media such as, for instance the liquids present in the proximal part of the small intestine, where dissolution of the proton pump inhibitor is desired. The NSAID(s) may be released in the stomach. The enteric coating layered pellets may further be covered with an overcoating layer before being formulated into the tablet and they may also contain one or more separating layer(s) in between the core material and the enteric coating layer.

Process

The process for the manufacture of the dosage form represents a further aspect of the invention. After formulation of the pellets by spray coating or layering of the proton pump inhibitor onto seeds, or by extrusion/spheronization or granulation, e.g. rotor granulation of homogeneous pellets, the pellets are first optionally covered with the separating layer(s) and then with the enteric coating layer(s) or a separating layer is spontaneously developed in situ between an alkaline core material and the enteric coating layer material. The coating is carried out as described above and in the accompanying examples. The preparation of the granules comprising the NSAID(s) and enteric coating layered NSAID pellets are also described above and in the examples. The pharmaceutical processes can preferably be completely water-based.

The enteric coating layered pellets, with or without an over-coat, are mixed with the prepared granules, tablet excipients and other pharmaceutical acceptable additives and compressed into tablets. Alternatively, the different active substances in the form of powders may be intimately dry mixed with tablet excipients, wet massed and compressed into conventional tablets before applying an optional separating layer and an enteric coating layer. The NSAID(s) may also be incorporated in a coating layer applied onto a multiple unit dosage form comprising the proton pump inhibitor, or the NSAID(s) and proton pump inhibitor in the form of enteric coating layered pellets are mixed with inactive tablet excipients and compressed into a multiple unit tableted dosage form.

The different active substances may also be formulated into different layers, wherein the layer comprising the NSAID(s) may be in the form of a control release preparation.

As a further alternative, the acid susceptible proton pump inhibitor in the form of enteric coating layered pellets may be filled in a capsule together with the NSAID(s) in the form of granules or enteric coating layered pellets, and optionally mixed with pharmaceutical excipients.

Use of the Preparation

The dosage forms according to the invention are especially advantageous in the treatment of gastrointestinal side-effects caused by NSAID(s), such as in a continuous treatment with NSAID(s). The new dosage forms are administered one to several times a day, preferably once or twice daily. The typical daily dose of the active substances varies and will depend on various factors such as the individual requirements of the patients, the mode of administration and disease. In general each dosage form will comprise 0, 1-200 mg of the proton pump inhibitor and 0, 1-1 000 mg of the NSAID(s). Preferably, each dosage form will comprise 10-80 mg of the proton pump inhibitor and 10-800 mg of the NSAID(s), and more preferably 10-40 mg of proton pump inhibitor and 10-500 mg of the NSAID(s), respectively. Especially preferred combinations comprise for instance 10 mg omeprazole together with 50 mg diclofenac, 10 mg omeprazole and 250 mg naproxen, 10 mg omeprazole and 10 mg piroxicam, or 10 mg omeprazole and 400 mg ibuprofen.

The multiple unit tablet preparation may also be suitable for dispersion in an aqueous liquid with slightly acidic pH-value before being orally administered or fed through a nasogastric tube.

The invention is illustrated more in detail in the following examples.

EXAMPLES

Example 1

Fast disintegrating multiple unit tableted dosage form comprising magnesium omeprazole and ibuprofen.

| Core material | |
|---|---|
| Magnesium omeprazole | 12.00 kg |
| Non-pareil cores | 12.00 kg |
| Hydroxypropyl methylcellulose | 1.8 kg |
| Water purified | 35.4 kg |
| Separating layer | |
| Core material (acc. to above) | 23.50 kg |
| Hydroxypropyl cellulose | 2.35 kg |
| Talc | 4.03 kg |
| Magnesium Stearate | 0.34 kg |
| Water purified | 48.00 kg |
| Enteric coating layer | |
| Pellets with sep layer (acc. to above) | 29.00 kg |
| Methacrylic acid copolymer (30% suspension) | 38.70 kg |
| Triethyl citrate | 3.48 kg |
| Mono- and diglycerides (NF) | 0.58 kg |
| Polysorbate 80 | 0.06 kg |
| Water purified | 22.68 kg |
| Over-coating layer | |
| Enteric coating layered pellets (acc. to above) | 44.7 kg |
| Hydroxypropyl methylcellulose | 0.58 kg |
| Mg-Stearate | 0.017 kg |
| Water purified | 11.6 kg |
| Tablets | mg/tablet |
| Over-coated pellets comprising omeprazole | 47.85 |
| Ibuprofen | 400 |

-continued

| | |
|---|---|
| Microcrystalline cellulose (MCC) | 273.6 |
| Polyvinylpyrrolidone cross-linked | 100.4 |
| Polyvinylpyrrolidone K-25 | 33.3 |
| Sodium laurylsulphate | 26.7 |
| Water purified | 297 |
| Sodium stearyl fumarate | 4.0 |

Suspension layering was performed in a fluid bed apparatus. Magnesium omeprazole was sprayed onto inert non-pareil cores from a water suspension containing the dissolved binder.

The prepared core material was coating layered with a separating layer in a fluid bed apparatus with a hydroxypropyl cellulose solution containing talc and magnesium stearate. The enteric coating layer consisting of methacrylic acid copolymer, mono- and diglycerides, triethylcitrate and polysorbate was sprayed onto the pellets (layered with a separating layer) in a fluid bed apparatus. In the same of apparatus the enteric coating layered pellets were coated with hydroxypropyl methylcellulose/Mg-Stearate suspension. The obtained pellets were classified by sieving.

Tablet granulation liquid was made by dissolving 26.7 parts of sodium laurylsulphate and 33.3 parts of polyvinylpyrrolidone K-25 in 267 parts of purified water. 400 parts of ibuprofen, 226 parts of the MCC and 10.4 parts of the cross-linked polyvinylpyrrolidone were dry-mixed. The granulating liquid was added to the powder mixture and the mass wet-mixed. 30 parts of water was added as quantum satis.

The wet mass was dried in an oven at 60° C. for approx. 6 hrs. The dried granules were milled to pass a 0.8 mm sieve.

The enteric coating layered omeprazole pellets, the milled ibuprofen granules, 47.6 parts of MCC, 4.0 parts sodium stearylfumarate and 90 parts of crosslinked polyvinylpyrrolidone were mixed and compressed to tablets on a tableting machine equipped with 15 mm diameter punches. Hardness of the 886 mg tablets tested with a Schleuniger apparatus varied between 5.3 and 5.9 kP. Disintegration time tested in simulated gastric juice (USP, without enzymes) was 49-52 sec (n=2).

Example 2

Fast disintegrating multiple unit tableted dosage form comprising S-omeprazole magnesium salt and naproxen.

| | |
|---|---|
| Core material | |
| S-omeprazole magnesium | 120 g |
| Non-pareil cores | 150 g |
| Polysorbat 80 | 2.4 g |
| Hydroxypropyl methylcellulose | 18 g |
| Water purified | 562 g |
| Separating layer | |
| Core material (acc. to above) | 200 g |
| Hydroxypropyl cellulose | 30 g |
| Talc | 51.4 g |
| Magnesium Stearate | 4.3 g |
| Water purified | 600 g |
| Enteric coating layer | |
| Pellets with sep layer (acc. to above) | 250 g |
| Methacrylic acid copolymer 30% suspension | 333.7 g |
| Triethyl citrate | 30 g |
| Mono- and diglycerides (NF) | 5.0 g |

-continued

| | |
|---|---|
| Polysorbate 80 (=Tween 80) | 0.5 g |
| Water purified | 195.8 g |
| Over-coating layer | |
| Enteric coating layered pellets | 371 g |
| Carboxymethylcellulose-sodium | 5.0 g |
| Water purified | 191 g |

| Tablets | mg/tablet |
|---|---|
| Over-coated pellets comprising S-omeprazole Mg-salt | 55 |
| Naproxen | 250 |
| Microcrystalline cellulose (MCC) | 150 |
| Hydroxypropylcellulose, low substituted | 40 |
| Polyvinylpyrrolidone K-90 | 5.0 |
| Water purified | 250 |

Suspension layering was performed in a fluid bed apparatus. S-omeprazole magnesium salt was sprayed onto inert sugar seeds (non-pareil cores) from a water suspension containing the dissolved binder and polysorbate 80.

The prepared core material was coating layered by a separating layer in a fluid bed apparatus with a hydroxypropyl cellulose solution containing talc and magnesium stearate. The enteric coating layer consisting of methacrylic acid copolymer, mono- and diglycerides, triethylcitrate and polysorbate was sprayed onto the pellets (with separating layer) in a fluid bed apparatus. In the same type of apparatus the enteric coating layered pellets were covered with carboxymethylcellulose-sodium solution. The over-coating layered pellets were classified by sieving.

5 parts of polyvinylpyrrolidone K-90 was dissolved in 150 parts of purified water to form the granulation liquid. Naproxen, MCC, and low-substituted hydroxypropyl cellulose were dry-mixed. The granulating liquid was added to the powder mixture and the mass wet-mixed. 100 parts of water was added as quantum satis.

The wet mass was dried in an oven at 60° C. for approx. 5-6 hrs. The dried granules were milled to pass a 1.0 mm sieve.

The enteric coating layered pellets and the milled granules were mixed and compressed to tablets on a tableting machine equipped with 18×8.5 mm punches. Average hardness for the 500 mg tablets tested (across the longest axis) with a Schleuniger apparatus was 9.4 kP. Disintegration time tested in purified water at 37° C. was 15-30 sec (n=2).

Example 3

Fast disintegrating multiple unit tableted dosage form comprising pantoprazole and piroxicam-β-hydroxypropyl-cyclodextrin.

| | |
|---|---|
| Core material | |
| Pantoprazole | 100 g |
| Non-pareil cores | 200 g |
| Hydroxypropylcellulose LF | 25 g |
| Water purified | 607 g |
| Separating layer | |
| Core material (acc. to above) | 200 g |
| Hydroxypropyl cellulose LF | 20 g |
| Talc | 34.3 g |
| Magnesium Stearate | 2.9 g |
| Water purified | 400 g |

-continued

| Enteric coating layer | |
|---|---|
| Pellets with sep layer (acc. to above) | 200 g |
| Methacrylic acid copolymer, 30% suspension | 333 g |
| Triethyl citrate | 30 g |
| Mono- and diglycerides (NF) | 5 g |
| Polysorbate 80 | 0.5 g |
| Water purified | 281.5 g |

| Tablets | mg/tablet |
|---|---|
| Pellets comprising pantoprazole | 133 |
| Piroxicam | 20 |
| β-hydroxypropyl-cyclodextrin, (90%) | 72 |
| Microcrystalline cellulose (MCC) | 276 |
| Polyvinylpyrrolidone cross-linked | 36.8 |
| Water purified | ≦2 |
| Sodium stearylfumarate (SSF) | 3.9 |

Suspension layering was performed in a fluid bed apparatus. Pantoprazole was sprayed onto inert sugar seeds (non-pareil cores) from a water suspension containing the dissolved binder.

The prepared core material was coating layered by a separating layer in a fluid bed apparatus with a hydroxypropyl cellulose solution containing talc and magnesium stearate. The enteric coating layer consisting of methacrylic acid copolymer, mono- and diglycerides, triethylcitrate and polysorbate was sprayed onto the pellets (with a separating layer) in a fluid bed apparatus. The pellets were classified by sieving.

The piroxicam was added to β-hydroxypropyl-cyclodextrin during mechanical treatment and moisturization with the water. The mass was dried in a drying oven at 50° C. and then milled to pass a 0.8 mm sieve.

The piroxicam-β-hydroxypropyl-cyclodextrin, the MCC, the cross-linked polyvinylpyrrolidone and the SSF were dry-mixed and thereafter this mixture was mixed with the pantoprazole pellets.

Compression to tablets was done on a tableting machine equipped with 18×8.5 mm punches. Average hardness for the, 577 mg tablets tested with a Schleuniger apparatus was 16.7 kP with variation between 14.8 and 18.7 kP, measurement taken along the longest axis. Disintegration time tested in water was approx. 4 minutes.

The tablets were coated with a pigmented dispersion like in Ex. 7.

Example 4

Two-layered tablet dosage form with fast disintegrating part having 20 mg of lansoprazole in the form of enteric coated pellets comprised in one layer, and the other layer being an extended release part designed as a hydrophilic gel matrix comprising 250 mg of naproxen.

Lansoprazole Enteric Coated Pellets

| Core material | |
|---|---|
| Lansoprazole | 400 g |
| Non-pareil cores | 400 g |
| Hydroxypropyl methylcellulose | 80 g |
| Sodium laurylsulphate | 3 g |
| Water purified | 1360 g |

-continued

| Sub-coating | |
|---|---|
| Core material (acc. to above) | 100 g |
| Hydroxypropyl methylcellulos | 9 g |
| Polyethyleneglycol 6000 | 1 g |
| Talc | 18 g |
| Ethanol 95% | 250 g |
| Water purified | 250 g |

| Enteric coating | |
|---|---|
| Sub-coated pellets (acc. to above) | 100 g |
| Hydroxypropyl methylcellulose phtalate | 39.9 g |
| Acetyltributyl citrate | 8 g |
| Cetanol | 2.1 g |
| Ethanol 95% | 162 g |
| Acetone | 378 g |

Suspension layering was performed in a fluid bed apparatus. Lansoprazole was sprayed onto inert non-pareil cores from a water suspension containing the dissolved binder and the wetting agent.

The prepared core material was sub-coated in a Wurster equipped fluid bed apparatus with the talc suspended in a HPMC/PEG-solution. PEG also have a function as plasticizer for the HPMC.

Enteric coating was performed in the same equipment with a solution in organic solvents of the materials forming the enteric layer.

| Tablets | mg/tablet |
|---|---|
| Pellets comprising lansoprazole | 94 |
| Microcrystalline cellulose | 181.8 |
| Polyvinyl pyrrolidone cross-linked | 18.2 |
| Naproxen | 250 |
| Polyoxyethylene (mwt appr. 4000000) | 200 |
| Sodium aluminium silicate | 50 |
| L-Arginine | 190 |
| Ethanol 95% (w/v) approx. | 280 |

Naproxen, Polyox WSR 301®, L-Arginin and sodium aluminum silicate were dry-mixed. The granulating liquid, ethanol, was added to the powder mixture and the mass wet-mixed. The wet mass was dried in an oven at 60° C. for approx. 8 hrs. The dried granules were milled to pass a 1.0 mm sieve.

Tablet compression was made by first pre-compressing 690 mg of the naproxen-containing granules and then filling 281 mg of a mixture consisting of 81 mg lansoprazole pellets plus 181.8 mg of MCC and 18.2 mg of crosslinked polyvinylpyrrolidone per tablet, on top. These materials were then compressed together to give the two-layered tablets on a Diaf tableting machine equipped with 9×20 mm punches. Tablet hardness tested with a Schleuniger apparatus over the longest axis was approximately 14 kP.

Naproxen dissolution-was tested in phosphate buffer pH 6.8. Obtained results;
1 hrs 14% dissolved
3 hrs 34% "
5 hrs 58% "
7 hrs 79% "
24 hrs 102% "

Example 5

Fast disintegrating multiple unit tableted dosage form comprising magnesium omeprazole and piroxicam.

| Core material (omeprazole) | |
|---|---|
| Magnesium omeprazole | 5.00 kg |
| Non-pareil cores | 10.00 kg |
| Hydroxypropyl methylcellulose | 0.75 kg |
| Water purified | 19.65 kg |
| Separating layer (omeprazole) | |
| Core material (acc. to above) | 14.60 kg |
| Hydroxypropyl cellulose | 1.46 kg |
| Talc | 2.5 kg |
| Magnesium Stearate | 0.21 kg |
| Water purified | 29.2 kg |
| Enteric coating layer (omeprazole) | |
| Pellets with sep layer(acc. to above) | 9.00 kg |
| Methacrylic acid copolymer (30% suspension) | 15.00 kg |
| Triethyl citrate | 1.35 kg |
| Mono- and diglycerides (NF) | 0.22 kg |
| Polysorbate 80 | 0.02 kg |
| Water purified | 8.8 kg |
| Over-coating layer (omeprazole) | |
| Enteric coating layered pellets | 9.0 kg |
| Hydroxypropyl methylcellulose | 0.18 kg |
| Mg-Stearate | 0.005 kg |
| Water purified | 3.6 kg |

Suspension layering was performed in a fluid bed apparatus. Magnesium omeprazole was sprayed onto inert sugar seeds (non-pareil cores) from a water suspension containing the dissolved binder.

The prepared core material was coating layered by a separating layer in a fluid bed apparatus with a hydroxypropyl cellulose solution containing talc and magnesium stearate. The enteric coating layer consisting of methacrylic acid copolymer, mono- and diglycerides, triethylcitrate and polysorbate was sprayed onto the sub-coated pellets in a fluid bed apparatus. In the same type of apparatus the enteric coating layered pellets were covered with hydroxypropyl methylcellulose/Mg-Stearate suspension. The over-coating layered pellets were classified by sieving.

| Core material (piroxicam) | |
|---|---|
| Piroxicam micronized | 35 g |
| Sugar seeds | 100 g |
| Hydroxypropyl methylcellulose 6 cps | 25 g |
| Water purified | 250 g |
| Ethanol 99% (w/v) | 250 g |
| Enteric coating layer (piroxicam) | |
| Piroxicam pellets (acc. to above) | 100 g | were coated with a suspension of the following composition to give a product with a content of 163 mg/g;

| Hydroxypropyl methylcellulose acetatesuccinate LF | 14.38 parts |
|---|---|
| Triethyl citrate | 2.87 parts |
| Sodium laurylsulphate | 0.43 parts |
| Talc | 4.32 parts |
| Water purified | 183.3 parts |

Suspension layering was performed in a fluid bed apparatus. Micronized piroxicam was sprayed onto inert non-pareil cores from a water suspension containing the dissolved binder.

The enteric coating layer consisting of hydroxypropyl methylcellulose acetatesuccinate, triethylcitrate, sodium laurylsulphate and talc was sprayed onto the piroxicam pellets in a fluid bed apparatus.

| Tablets (for 1000 pcs) | |
|---|---|
| pellets comprising omeprazole | 95.7 g |
| pellets containing piroxicam | 122.7 g |
| Microcrystalline cellulose (MCC) | 240 g |
| Polyvinylpyrrolidone cross-linked (PVP-XL) | 20 g |
| Hydroxypropylcellulose, low-substituted (L-HPC) | 40 g |
| Sodium stearylfumarate (SSF) | 4.6 g |

MCC, L-HPC and PVP-XL were mixed together until homogenity. The two kind of enteric coating layered pellets were admixed thereafter. Finally the lubricant SSF was admixed and this mixture was compressed to tablets on a tableting machine equipped with 8.5×16 mm punches. Hardness of the 523 mg tablets tested with a Schleuniger apparatus varied between 8 and 9 kP. Disintegration time tested in water 37° C. was less than 1 minute.

The tablets were coated with a pigmented dispersion like in Example 7.

Example 6

Fast disintegrating enteric coating layered tablet comprising magnesium omeprazole and diclofenac.

| Tablets (for 2000 pcs) | |
|---|---|
| Omeprazole magnesium (corr. 20 mg omeprazole) | 45.0 g |
| Diclofenac sodium (corr. 20 mg diclofenac) | 43.2 g |
| Microcrystalline cellulose (MCC) | 110 g |
| Polyvinylpyrrolidone cross-linked (PVP-XL) | 50 g |
| Hydroxypropylcellulose, low-substituted (L-HPC) | 50 g |
| Sodium stearylfumarate (SSF) | 8.6 g |
| Water purified approx. | 170 g |

The omeprazole, diclofenac, MCC, L-HPC, 30 grams of PVP-XL and 5.6 grams of SSF were mixed and then the water was added during continuously mixing. The granulate was dried in a drying oven at 60° C. for approx. 1.5 hours. The dry granulate was milled to pass sieve 1.0 mm.

The milled granules were mixed with 20 grams of PVP-XL and 3.0 grams of SSF. This mixture was compressed to 153 mg tablets on a tableting machine using 7 mm diameter punches. Average tablet hardness was 7.4 kP (n=6). Disintegration time in water 37° C. was 1 minute 20 seconds (n=1).

The tablets were coating layered with a separating layer consisting of hydroxypropyl methylcellulose (HPMC) and talc in a Wurster equipped fluidized bed.

| Application of separating layer | |
|---|---|
| Tablets 7 mm | 100.1 g |
| coating dispersion; | |
| HPMC 6 cps | 5.5 g |
| Talc | 1.15 g |
| EtOH 99%(w/v) | 46.7 g |
| Water purified | 46.7 g |

The obtained coating layered tablets were further coating layered by an enteric coating layer in the same apparatus.

| Application of enteric coating layer | |
|---|---|
| Tablets with separating layer | 100 g |
| coating dispersion; | |
| Methacrylic acid copolymer as 30% suspension | 26.4 g (7.92 g dry mtrl.) |
| Polyethyleneglycole 400 | 0.9 g |
| Titanium dioxide | 0.83 g |
| Iron oxide reddish brown | 0.28 g |
| Water purified | 55.1 g |

The weight increase of the tablets in the enteric coating step was approx. 11 mg/tablet, corresponding to approx. 7% of the weight of charged tablets.

The pigments in the enteric coating layer provides protection against light.

Example 7

Fast disintegrating multiple unit tableted dosage form comprising magnesium omeprazole and an inner coating layer comprising diclofenac-sodium and an outer pigmented coating layer providing light protection.

Magnesium omeprazole enteric coating layered pellets from Ex. 5.

| Tablets | mg/tablet |
|---|---|
| Pellets comprising omeprazole | 83.3 |
| Microcrystalline cellulose (MCC) | 181.4 |
| Polyvinylpyrrolidone cross-linked | 3.7 |
| Sodium stearyl fumarate (SSF) | 0.4 |

Pellets were prepared as in Example 5.

The MCC, the cross-linked polyvinylpyrrolidone and the omeprazole containing pellets were dry-mixed. Thereafter the SSF was admixed.

The mixture was compressed to tablets on a tableting machine equipped with 9 mm diameter punches. Hardness of the 269 mg tablets tested with a Schleuniger apparatus varied between 8 and 9 kP.

The tablets were coated in a fluidized bed with the solution below, until average tablet weight was 298 mg.

| Diclofenac-sodium | 20.0 parts by weight |
|---|---|
| HPMC 6 cps | 11.4 parts by weight |
| EtOH 99% (w/v) | 113.6 parts by weight |
| Water purified | 113.6 parts by weight |

Finally these tablets were covered with pigmented suspension in the same equipment. The composition of the coating suspension was;

| HPMC 6 cps | 10 parts by weight |
|---|---|
| Polyethylene glycol mwt 6000 | 2.5 parts by weight |
| TiO$_2$ | 1.83 parts by weight |
| Iron oxide yellow | 0.40 parts by weight |
| EtOH 99% (w/v) | 85 parts by weight |
| Water purified | 85 parts by weight |

Obtained average tablet weight was 303 mg. Disintegration time tested in water 37° C. was less than 4 minutes (n=4).

Example 8

A capsule formulation comprising magnesium omeprazole and piroxicam.

| Capsules | |
|---|---|
| Enteric coating layered omeprazole pellets (manufacturing and composition as in Ex. 5) | 95.7 mg/cap |
| Enteric coating layered piroxicam pellets (manufacturing and composition as in Ex. 5) | 122.7 mg/cap |

Prepared pellets are filled into hard gelatine capsules, size 3. Optionally a small amount of lubricant is added before filling into capsules. The amount of omeprazole in each capsule is approx. 20 mg and the amount of piroxicam is approx. 20 mg.

Example 9

A capsule formulation comprising S-omeprazole magnesium salt and naproxen.

| Capsules | |
|---|---|
| Enteric coating layered pellets (manufacturing and composition as in Ex. 2) | 55.2 mg/cap |
| Naproxen granulation (manufacturing and composition as in Ex. 2) | 445 mg/cap |

Prepared granules and enteric coating layered pellets are filled into hard gelatine capsules, size 00. Optionally a small amount of lubricant is added before filling into capsules. The amount of S-omeprazole in each capsule is approx. 10 mg and the amount of naproxen is approx. 250 mg.

Example 10

Fast disintegrating multiple unit tableted dosage form comprising magnesium omeprazole and diclofenac-Na.

| Core material | |
|---|---|
| Magnesium omeprazole | 5 kg |
| Sugar sphere seeds | 10 kg |
| Hydroxypropyl methylcellulose | 0.75 kg |
| Water purified | 19.7 kg |
| Separating layer | |
| Core material | 10.2 kg |
| Hydroxypropyl cellulose | 1.02 kg |
| Talc | 1.75 kg |
| Magnesium stearate | 0.146 kg |
| Water purified | 21.4 kg |
| Enteric coating layer | |
| Pellets covered with separating layer | 11.9 kg |
| Methacrylic acid copolymer (30% suspension) | 19.8 kg |
| Triethyl citrate | 1.79 kg |
| Mono- and diglycerides (NF) | 0.297 kg |
| Polysorbate 80 | 0.03 kg |
| Water purified | 11.64 kg |
| Over-coating layer | |
| Enteric coating layered pellets | 20.0 kg |
| Hydroxypropyl methylcellulose | 0.238 kg |

| -continued | |
|---|---|
| Magnesium stearate | 0.007 kg |
| Water purified | 6.56 kg |
| Tablets | mg/tablet |
| Overcoated pellets comprising omeprazole | 82.4 |
| Diclofenac-Na | 50.0 |
| Microcrystalline cellulose (MCC) | 261 |
| Polyvinylpyrrolidone cross-linked | 5.6 |
| Sodium stearyl fumarate | 0.56 |

Suspension layering was performed in a fluid bed apparatus. Magnesium omeprazole was sprayed onto sugar sphere seeds from a water suspension containing the dissolved binder. The size of sugar sphere seeds were in the range of 0.25 to 0.35 mm. The prepared core material was covered with a hydroxypropyl cellulose solution containing talc and magnesium stearate. The enteric coating layer consisting of methacrylic acid copolymer, mono- and diglycerides, triethyl citrate and polysorbate was sprayed onto the pellets covered with a separating layer in a fluid bed apparatus. In a fluid bed apparatus enteric coating layered pellets were coated with a hydroxypropyl methylcellulose solution containing magnesium stearate. The over-coating layered pellets were classified by sieving.

The enteric coating layered pellets with an over-coating layer, diclofenac-Na, MCC, polyvinylpyrrolidone cross-linked and sodium stearyl fumarate were dry mixed and compressed into tablets using an excenter tableting machine equipped with 11 mm punches. The amount of omeprazole in each tablet was approx. 10 mg and the amount of diclofenac-Na was approx. 50 mg. The tablet hardness was measured to 80 N.

Example 11

Fast disintegrating multiple unit tableted dosage form comprising magnesium omeprazole and piroxicam.

| Core material | |
|---|---|
| Magnesium omeprazole | 10.0 kg |
| Sugar sphere seed | 10.0 kg |
| Hydroxypropyl methylcellulose | 1.5 kg |
| Water purified | 29.9 kg |
| Separating layer | |
| Core material | 20.0 kg |
| Hydroxypropyl cellulose | 2.0 kg |
| Talc | 3.43 kg |
| Magnesium stearate | 0.287 kg |
| Water purified | 41.0 kg |
| Enteric coating layer | |
| Pellets covered with separating layer | 24.5 kg |
| Methacrylic acid copolymer (30% suspension) | 32.7 kg |
| Triethyl citrate | 2.94 kg |
| Mono- and diglycerides (NF) | 0.49 kg |
| Polysorbate 80 | 0.049 kg |
| Water purified | 19.19 kg |
| Over-coating layer | |
| Enteric coating layered pellets | 37.8 kg |
| Hydroxypropyl methylcellulose | 0.49 kg |
| Magnesium stearate | 0.0245 kg |
| Water purified | 11.6 kg |

| -continued | |
|---|---|
| Tablets | mg/tablet |
| Overcoated pellets comprising omeprazole | 94.9 |
| Piroxicam | 20.0 |
| Microcrystalline cellulose (MCC) | 280 |
| Polyvinylpyrrolidone cross-linked | 5.6 |
| Sodium stearyl fumarate | 0.56 |

Enteric coating layered pellets of magnesium omeprazole with an overcoating layer were prepared as in Example 10.

The enteric coating layered pellets with an over-coating layer, piroxicam, MCC, polyvinylpyrrolidone cross-linked and sodium stearyl fumarate were dry mixed and compressed into tablets using an excenter tableting machine equipped with 11 mm punches. The amount of omeprazole in each tablet was approx. 20 mg and the amount of piroxicam was approx. 20 mg. The tablet hardness was measured to 110 N.

Results

| | "Acid resistance" i.e. % left after exposure to 0.1 N HCl for 2 hrs |
|---|---|
| | Tablets |
| Ex 1 | 95% |
| Ex 2 | 95% |
| Ex 3 | 99% |
| Ex 4 | 91% |
| Ex 5 | 92% |
| Ex 6 | 96% |
| Ex 7 | 93% |
| Ex 10 | 91% |
| Ex 11 | 91% |

The best mode to practice the present invention is according to the dosage forms of the types described in examples 5, 7 and 10.

The enteric coating layered pellets comprising a proton pump inhibitor may also be prepared as described in the following examples.

Example 12

Preparation of enteric coating layered pellets by extrusion/spheronization.

| Core material | |
|---|---|
| Magnesium omeprazole | 600 g |
| Mannitol | 1000 g |
| Microcrystalline cellulose | 300 g |
| Hydroxypropyl cellulose | 100 g |
| Sodium lauryl sulphate | 6 g |
| Water purified | 802 g |
| Separating layer | |
| Core material (acc. to above) | 400 g |
| Hydroxypropyl methylcellulose | 48 g |
| Water purified | 960 g |
| Enteric coating layer | |
| Pellets covered with separating layer (acc. to above) | 200 g |
| Methacrylic acid copolymer | 100 g |
| Triethyl citrate | 30 g |
| Mono- and diglycerides (NF) | 5 g |

-continued

| | |
|---|---|
| Polysorbate 80 | 0.5 g |
| Water purified | 309 g |

Sodium lauryl sulphate is dissolved in purified water to form the granulation liquid. Magnesium omeprazole, mannitol, microcrystalline cellulose and hydroxypropyl cellulose are dry-mixed. The granulation liquid is added to the powder mixture and the mass is wet-mixed.

The wet mass is forced through an extruder equipped with screens of size 0.5 mm. The extrudate is spheronized on a friction plate in a spheronizing apparatus. The core material is dried in a fluid bed dryer and classified. The prepared core material is covered by a separating layer in a fluid bed apparatus with a hydroxypropyl methylcellulose/water solution.

The enteric coating layer is applied to the pellets covered with separating layer from an aqueous dispersion of methacrylic acid copolymer plasticized with triethyl citrate to which a mono- and diglycerides/polysorbate dispersion has been added. The pellets are dried in a fluid bed apparatus.

Example 13

Preparation of enteric coating layered pellets by powder layering of sugar sphere seeds.

| | |
|---|---|
| Core material | |
| Magnesium omeprazole | 1.500 g |
| Sugar sphere seeds | 1.500 g |
| Hydroxypropyl methylcellulose | 420 g |
| Aerosil® | 8 g |
| Water purified | 4.230 g |
| Separating layer | |
| Core material (acc. to above) | 500 g |
| Hydroxypropyl cellulose | 40 g |
| Talc | 67 g |
| Magnesium stearate | 6 g |
| Water purified | 800 g |
| Enteric coating layer | |
| Pellets covered with separating layer (acc. to above) | 500 g |
| Methacrylic acid copolymer | 200 g |
| Triethyl citrate | 60 g |
| Water purified | 392 g |

Magnesium omeprazole, part of the hydroxypropyl methylcellulose and Aerosil® are dry-mixed forming a powder. Sugar sphere seeds (0.25-0.40 mm) are layered with the powder in a centrifugal fluidized coating granulator while spraying a hydroxypropyl methylcellulose solution (6%, w/w).

The prepared core material is dried and covered by a separating layer in a centrifugal fluidized coating-granulator. A fluid bed apparatus is used for enteric coating layereing.

Example 14

Preparation of enteric coating layered pellets with cores of silicon dioxide seeds.

| | |
|---|---|
| Core material | |
| Magnesium omeprazole | 8.00 kg |
| Silicon dioxide | 8.00 kg |
| Hydroxypropyl methylcellulose | 1.41 kg |
| Sodium lauryl sulphate | 0.08 kg |
| Water purified | 28.00 kg |

-continued

| | |
|---|---|
| Separating layer | |
| Core material (acc. to above) | 10.00 kg |
| Hydroxypropyl methylcellulose | 0.80 kg |
| Water purified | 10.00 kg |
| Enteric coating layer | |
| Pellets covered with separating layer (acc. to above) | 300 g |
| Methacrylic acid copolymer | 124 g |
| Polyethylene glycol 400 | 25 g |
| Mono- and diglycerides (NF) | 3 g |
| Polysorbate 80 | 1 g |
| Water purified | 463 g |

Suspension layering is performed in a fluid bed apparatus. Magnesium omeprazole is sprayed onto the silicon dioxide seeds from a water suspension containing the dissolved binder and a surface active ingredient.

The prepared core material is covered with a separating layer in a fluid bed apparatus with a hydroxypropyl methylcellulose solution. The enteric coating layer consisting of methacrylic acid copolymer, mono- and diglycerides, polyethylene glycol 400 and polysorbate is sprayed onto the pellets covered with separating layer in a fluid bed apparatus.

Example 15

Preparation of enteric coating layered pellets.

| | |
|---|---|
| Enteric coating layer | |
| Pellets covered with separating layer (manufacturing and composition as in example 12) | 500 g |
| Methacrylic acid copolymer | 250 g |
| Polyethylene glycol 6000 | 75 g |
| Mono- and diglycerides (NF) | 12.5 g |
| Polysorbate 80 | 1.2 g |
| Water purified | 490 g |

Example 16

Preparation of enteric coating layered pellets.

| | |
|---|---|
| Enteric coating | |
| Pellets covered with separating layer (manufacturing and composition as in example 1) | 500 g |
| Hydroxypropyl methylcellulose phthalate | 250 g |
| Cetanol | 50 g |
| Ethanol (95%) | 1000 g |
| Acetone | 2500 g |

Example 17

Preparation of enteric coating layered pellets.

| | |
|---|---|
| Core material | |
| Omeprazole | 225 g |
| Mannitol | 1425 g |
| Hydroxypropyl cellulose | 60 g |

| -continued | |
|---|---|
| Microcrystalline cellulose | 40 g |
| Lactose anhydrous | 80 g |
| Sodium lauryl sulphate | 5 g |
| Disodium hydrogen phosphate dihydrate | 8 g |
| Water purified | 350 g |
| Separating layer | |
| Core material (acc. to above) | 300 g |
| Hydroxypropyl cellulose | 30 g |
| Talc | 51 g |
| Magnesium stearate | 4 g |
| Enteric coating layer | |
| Pellets covered with separating layer (acc. to above) | 300 g |
| Methacrylic acid copolymer | 140 g |
| Triethyl citrate | 42 g |
| Mono- and diglycerides (NF) | 7 g |
| Polysorbate 80 | 0.7 g |

The dry ingredients for producing the core material are well nixed in a mixer. Addition of granulation liquid is made and the mixture is kneaded and granulated to a proper consistency. The wet mass is pressed through an extruder screen and the granules are converted into a spherical form in a spheronizer. The core material is dried in a fluid bed apparatus and classified into a suitable particle size range, e.g. 0.5-1.0 mm. The prepared core material is covered with a separating layer and enteric coating layered as described in previous examples.

Preparation of active substance.

Magnesium omeprazole used in some of the examples is produced according to the process described in WO/95/01977, the single enantiomers of omeprazole salts are prepared as described in WO/94/27988 and omeprazole is produced according to the process disclosed in EP-A1 0005129. These documents are hereby incorporated in a whole by reference.

The invention claimed is:

1. A tablet formulation comprising:
   (a) as a first component, an acid susceptible proton pump inhibitor,
   (b) as a separate second component, at least one Non Steroidal Antiinflammatory Drug (NSAID), and
   (c) as an optional third component, one or more pharmaceutically acceptable excipients,
wherein the first component is protected by an enteric coating layer, and wherein the second component is separated from the first component by the enteric coating layer protecting the first component.

2. The tablet formulation according to claim 1, further comprising a separating layer separating the enteric coating layer from the proton pump inhibitor.

3. The tablet formulation according to claim 1, wherein the tablet formulation comprises the proton pump inhibitor and one NSAID.

4. The tablet formulation according to claim 1, wherein the proton pump inhibitor is selected from the group consisting of omeprazole, an alkaline salt of omeprazole, a single enantiomer of omeprazole and an alkaline salt of the single enantiomer.

5. The tablet formulation according to claim 4, wherein the proton pump inhibitor is S-omeprazole magnesium salt.

6. The tablet formulation according to claim 1, wherein the proton pump inhibitor is selected from the group consisting of lansoprazole, a pharmaceutically acceptable salt of lansoprazole, a single enantiomer of lansoprazole and a pharmaceutically acceptable salt of the single enantiomer.

7. The tablet formulation according to claim 1, wherein the proton pump inhibitor is selected from the group consisting of pantoprazole, a pharmaceutically acceptable salt of pantoprazole, a single enantiomer of pantoprazole and a pharmaceutically acceptable salt of the single enantiomer.

8. The tablet formulation according to any one of claims 4-7, wherein the NSAID is selected from the group consisting of ibuprofen, diclofenac, piroxicam, naproxen and pharmaceutically acceptable salts thereof.

9. The tablet formulation according to any one of claims 4-7, wherein the NSAID is diclofenac or piroxicam, or a pharmaceutically acceptable salt thereof.

10. The tablet formulation according to claim 1, wherein the amount of the proton pump inhibitor is in the range of 10-80 mg and the amount of the NSAID is in the range of 10-800 mg.

11. The tablet formulation according to claim 1, wherein the amount of the proton pump inhibitor is in the range of 10-40 mg and the amount of the NSAID is in the range of 10-500 mg.

12. The tablet formulation according to claim 1, wherein the tablet formulation further comprises a first and second layer, and wherein the first layer comprises the first component and the second layer comprises the second component.

13. The tablet formulation according to claim 1, wherein the tablet formulation further comprises a first and second layer, and wherein the first layer comprises the proton pump inhibitor in the form of enteric coating layered pellets and tablet excipients, and the second layer comprises the NSAID.

14. The tablet formulation according to claim 1, wherein the proton pump inhibitor is in the form of enteric coating layered pellets compressed to a tablet which is covered by a layer comprising the NSAID.

15. The tablet formulation according to claim 14, wherein the layer comprising the NSAID is covered by a pigmented tablet filmcoating layer.

16. The tablet formulation according to claim 1, wherein the proton pump inhibitor is in the form of enteric coating layered pellets, and the NSAID is in the form of enteric coating layered pellets.

17. The tablet formulation according to claim 1, wherein the proton pump inhibitor is in the form of enteric coating layered pellets, and the NSAID is in the form of pellets coating layered with an extended release film.

18. A method for the treatment of gastrointestinal side-effects associated with NSAID treatment in mammals in need thereof by administering a therapeutically effective dose of the tablet formulation according to any one of claims 1, 2-12, 13, or 14-15.

19. The method according to claim 18, wherein the disorder is an upper gastrointestinal disorder associated with NSAID treatment.

20. The tablet formulation according to any one of claims 4-7, wherein the NSAID is a NO-releasing NSAID, salt, hydrate, or ester thereof.

21. The tablet formulation according to claim 20, wherein the NO-releasing NSAID is selected from the group consisting of NO-releasing diclofenac and NO-releasing naproxen.

22. The tablet formulation according to any one of claims 4-7, wherein the NSAID is acetyl salicylic acid.

23. The tablet formulation according to any one of claims 4-7, wherein the NSAID is a (COX)2 selective NSAID, salt, hydrate or ester thereof.

24. The tablet formulation according to claim 13, wherein the second layer gives an extended release of the NSAID.

25. The tablet formulation according to claim 24, wherein the second layer further comprises a gelling matrix giving an extended release of the NSAID.

26. The tablet formulation according to any one of claims 13, 14-17, 24 or 25 wherein the acid resistance of the enteric coating layered pellets comprising the proton pump inhibitor is in compliance with the requirements on enteric coating layered articles defined in the United States Pharmacopeia.

27. The tablet formulation according to any one of claims 13, 14-17, 24 or 25 wherein the acid resistance of the enteric coating layered pellets comprising the proton pump inhibitor does not decrease more than 10% during compression of the enteric coating layered pellets into the multiple unit tablet formulation.

28. The tablet formulation according to any one of claims 13, 14-17, 24 or 25 wherein the enteric coating layer of the individual pellets comprises a plasticizer.

* * * * *